(12) United States Patent
Rapoport et al.

(10) Patent No.: US 9,681,822 B2
(45) Date of Patent: Jun. 20, 2017

(54) MRI DEVICE WITH A PLURALITY OF INDIVIDUALLY CONTROLLABLE ENTRY PORTS AND INSERTS THEREFOR

(71) Applicant: ASPECT IMAGING LTD., Shoham (IL)

(72) Inventors: Uri Rapoport, Moshav Ben Shemen (IL); Itzchak Rabinovitz, Nes Ziona (IL)

(73) Assignee: ASPECT MAGNET TECHNOLOGIES LTD., Shoham (IL)

( * ) Notice: Subject to any disclaimer, the term of this patent is extended or adjusted under 35 U.S.C. 154(b) by 0 days.

(21) Appl. No.: 14/182,766

(22) Filed: Feb. 18, 2014

(65) Prior Publication Data
US 2014/0158062 A1 Jun. 12, 2014

Related U.S. Application Data

(62) Division of application No. 13/241,367, filed on Sep. 23, 2011, now Pat. No. 8,807,084.
(Continued)

(51) Int. Cl.
*A61B 5/055* (2006.01)
*G01R 33/30* (2006.01)
*A01K 29/00* (2006.01)

(52) U.S. Cl.
CPC .......... *A61B 5/0555* (2013.01); *A01K 29/005* (2013.01); *G01R 33/30* (2013.01)

(58) Field of Classification Search
USPC .......... 324/300–322; 600/407–435; 119/417, 119/751; 382/128–131
See application file for complete search history.

(56) References Cited

U.S. PATENT DOCUMENTS 5,066,915 A 11/1991 Omori et al.
5,167,160 A 12/1992 Hall, II
(Continued)

OTHER PUBLICATIONS

Aspect Imaging Ltd., "Shutting Assembly for Closing an Entrance of an MRI Device", co-pending U.S. Appl. No. 14/540,163, filed Nov. 13, 2014.
(Continued)

*Primary Examiner* — Melissa Koval
*Assistant Examiner* — Tiffany Fetzner
(74) *Attorney, Agent, or Firm* — Pearl Cohen Zedek Latzer Baratz LLP (57) ABSTRACT

An animal handling system for use in an MRD device, including: a first elongated enclosure having a proximal end, a distal open end and a first geometry, and a second first elongated enclosure having a proximal end, a distal open end and a second geometry. The first geometry comprises a first cross-sectional area which is larger than a second cross-sectional area of the second geometry. The first elongated enclosure is inserted into a first input port of the MRD device and the second elongated enclosure is inserted in a second input port of the MRD device diametrically opposite to second input port, such that on insertion of the first elongated enclosure into the first input port and insertion of the second elongated enclosure into the second input, the second elongated enclosure slides into the first elongated enclosure through the open distal end of the first elongated enclosure.

4 Claims, 6 Drawing Sheets

Related U.S. Application Data (60) Provisional application No. 61/387,992, filed on Sep. 30, 2010.

(56) References Cited

U.S. PATENT DOCUMENTS

| | | | |
|---|---|---|---|
| 5,490,513 A | 2/1996 | Damadian et al. | |
| 5,623,927 A | 4/1997 | Damadian et al. | |
| 7,414,403 B2* | 8/2008 | Chiodo | A61B 5/0555 324/318 |
| 7,784,429 B2* | 8/2010 | Chiodo | A61D 3/00 119/417 |
| 7,865,226 B2* | 1/2011 | Chiodo | A01K 1/0613 119/751 |
| 8,482,278 B2* | 7/2013 | Wolke | G01R 33/30 324/307 |
| 8,660,633 B2* | 2/2014 | Zagorchev | A61B 6/04 119/417 |
| 8,774,899 B2* | 7/2014 | Chiodo | A01K 1/0613 600/415 |
| 8,851,018 B2 | 10/2014 | Rapoport et al. | |
| 8,896,310 B2 | 11/2014 | Rapoport | |
| 8,918,163 B2* | 12/2014 | Yared | A61B 6/0421 600/407 |
| 2005/0027190 A1* | 2/2005 | Chiodo | A61B 5/0555 600/415 |
| 2005/0248349 A1 | 11/2005 | Okada et al. | |
| 2006/0145698 A1 | 7/2006 | Griffin | |
| 2007/0238946 A1* | 10/2007 | Chiodo | A01K 1/0613 600/407 |
| 2008/0072836 A1* | 3/2008 | Chiodo | A61D 3/00 119/417 |
| 2009/0000567 A1 | 1/2009 | Hadjioannou et al. | |
| 2010/0072999 A1* | 3/2010 | Wolke | G01R 33/30 324/309 |
| 2010/0100072 A1 | 4/2010 | Chiodo | |
| 2010/0198047 A1* | 8/2010 | Zagorchev | A61B 6/04 119/417 |
| 2010/0269260 A1 | 10/2010 | Lanz et al. | |
| 2011/0071388 A1* | 3/2011 | Yared | A61B 6/0421 600/425 |
| 2011/0092807 A1* | 4/2011 | Chiodo | A01K 1/0613 600/421 |
| 2011/0162652 A1 | 7/2011 | Rapoport | |
| 2011/0186049 A1 | 8/2011 | Rapoport | |
| 2011/0234347 A1 | 9/2011 | Rapoport | |
| 2011/0304333 A1 | 12/2011 | Rapoport | |
| 2012/0071745 A1 | 3/2012 | Rapoport | |
| 2012/0073511 A1 | 3/2012 | Rapoport et al. | |
| 2012/0077707 A1 | 3/2012 | Rapoport | |
| 2012/0119742 A1 | 5/2012 | Rapoport | |
| 2013/0079624 A1 | 3/2013 | Rapoport | |
| 2013/0109956 A1 | 5/2013 | Rapoport | |
| 2013/0237803 A1 | 9/2013 | Rapoport | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0099010 A1 | 4/2014 | Rapoport et al. | |
| 2014/0103927 A1 | 4/2014 | Rapoport | |
| 2014/0117989 A1 | 5/2014 | Rapoport | |
| 2014/0128725 A1 | 5/2014 | Rapoport et al. | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0257081 A1 | 9/2014 | Rapoport | |
| 2014/0266203 A1 | 9/2014 | Rapoport et al. | |
| 2014/0300358 A1 | 10/2014 | Rapoport | |
| 2014/0378821 A1 | 12/2014 | Rapoport et al. | |
| 2014/0378825 A1 | 12/2014 | Rapoport et al. | |
| 2015/0059655 A1 | 3/2015 | Rapoport | |
| 2015/0065788 A1 | 3/2015 | Rapoport | |

OTHER PUBLICATIONS

Aspect Imaging Ltd., "Cage in an MRD with Fastenting/Attenuating System", co-pending U.S. Appl. No. 14/527,950, filed Oct. 30, 2014.
Rapoport, Uri, "RF Shielding Conduit in an MRI Closure Assembly", co-pending U.S. Appl. No. 14/574,785, filed Dec. 18, 2014.
Aspect Imaging Ltd., "System and Method for Generating Invasively Hyperpolarized Images", co-pending U.S. Appl. No. 14/556,682, filed Dec. 1, 2014.
Aspect Imaging Ltd., "System and Method for Generating Invasively Hyperpolarized Images", co-pending U.S. Appl. No. 14/556,654, filed Dec. 1, 2014.
Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014.
Aspect Imaging Ltd., "Foamed Patient Transport Incubator", co-pending U.S. Appl. No. 14/531,289, filed Nov. 3, 2014.
Aspect Imaging Ltd., "Mechanical Clutch for MRI", co-pending U.S. Appl. No. 14/611,379, filed Feb. 2, 2015.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable NMR Probe Cassette and Methods Thereof", co-pending U.S. Appl. No. 14/504,890, filed Oct. 2, 2014.
Aspect Imaging Ltd., "NMR Extractable Probe Cassette Means and Methods Thereof", co-pending U.S. Appl. No. 14/504,907, filed Oct. 2, 2014.
Aspect Imaging Ltd., "Means for Operating an MRI Device Within a RF-Magnetic Environment", co-pending U.S. Appl. No. 14/596/320, filed Jan. 14, 2015.
Aspect Imaging Ltd., "Means and Method for Operating an MRI Device Within a RF-Magnetic Environment", co-pending U.S. Appl. No. 14/596,329, filed Jan. 14, 2015.
Aspect Imaging Ltd., "CT/MRI Integrated System for the Diagnosis of Acute Strokes and Methods Thereof", co-pending U.S. Appl. No. 14/598,517, filed Jan. 16, 2015.
Aspect Imaging Ltd., "RF Automated Tuning System Used in a Magnetic Resonance Device and Methods Thereof", co-pending U.S. Appl. No. 14/588,741, filed Jan. 2, 2015.
Aspect Imaging Ltd., "Method for Providing High Resolution, High Contrast Fused MRI Images", co-pending U.S. Appl. No. 13/877,533, filed Apr. 3, 2013.
Aspect Imaging Ltd., "Method for Manipulating the MRI's Protocol of Pulse-Sequences", co-pending U.S. Appl. No. 14/070,695, filed Nov. 4, 2013.
Aspect Imaging Ltd, "MRI-Incubator's Closure Assembly", co-pending U.S. Appl. No. 14/539,442, filed Nov. 12, 2014.
X.Josette Chen: "Mouse Morphological Phenotyping With Magnetic Resonance Imaging", Methods in Molecular Medicine, vol. 124, 2006, pp. 103-127, XP009155743.
Aspect Magnet Technologies: "Aspect Imaging Products (Technical Features) and Press Releases (Aspect Magnet Technologies Delivers Multiple New Compact MRI Systems)", , Aug. 31, 2010 (Aug. 31, 2010), XP002667774, Retrieved from the Internet: URL:http://www.aspectimaging.com/ [retrieved on Jan. 24, 2012].

(56) References Cited

OTHER PUBLICATIONS

P.J.Cassidy et al.: "An Animal Handling System for Small Animal in vivo MR", Proc.Intl.Soc.Mag.Reson.Med. 13, 2005, p. 2541, XP002667775.
European Serach Report for EP applicatoin No. 11182715 dated Feb. 2, 2012.
European Search Report for EP application No. 14188947.7 dated Jan. 22, 2015.

* cited by examiner

MRI DEVICE WITH A PLURALITY OF INDIVIDUALLY CONTROLLABLE ENTRY PORTS AND INSERTS THEREFOR

FIELD OF THE INVENTION

The present invention generally pertains to an MRI device with a plurality of individually controllable entry ports and inserts therefore, and to methods using the same.

BACKGROUND OF THE INVENTION

Magnetic resonance imaging (MRI), or nuclear magnetic resonance imaging (NMRI), is primarily a noninvasive medical imaging technique used in radiology to visualize detailed internal structure and limited function of the body.

Objects to be analyzed are positioned within an MRI device in a predefined specific location and configuration. It is advantageous to adjust the location of the animal under inspection within the MRI device to obtain optimal analysis. Few patents pertain to means and methods of positioning analyzed objects. Hence for example, U.S. Pat. No. 5,066,915 discloses an RF coil positioning device for an MRI device in which a pallet is movably mounted on a mount and is moved by a drive means so that an RF coil unit mounted on the pallet is moved from its initial position at an imaging position in a magnetostatic field generator, the coil positioning device comprising: coil detecting means provided at a predetermined position along a path of the pallet, for detecting the passage of the RF coil unit through a reference position on the path and generating a detection signal, the distance between the reference position and the imaging position being preknown; distance detecting means for detecting the distance of travel of the pallet; and drive control means supplied with signals from the coil detecting means and the distance detecting means, for controlling the drive means to move the pallet until the distance of its travel after the generation of the detection signal becomes equal to the distance from the reference position to the imaging position; wherein the coil detecting means is provided below the underside of the pallet. Likewise, US patent discloses a diagnostic table for a medical imaging apparatus, the table comprising: a supporting unit; a tabletop movably supported by the supporting unit; a sliding command input device configured to receive a sliding command input, and generate a sliding command instruction corresponding to the sliding command input; a driving device configured to slidably move the tabletop in response to the sliding command instruction; a detector configured to detect actual sliding movement of the tabletop; a controller configured to compare the actual sliding movement of the tabletop with the sliding command instruction, the controller being configured to generate a fault condition instruction when the actual sliding movement of the tabletop is inconsistent with the sliding command instruction; and a stopper provided on the supporting unit and configured to be activated in response to the fault condition instruction in order to inhibit sliding movement of the tabletop. The MRI operator in those MRI systems can not routinely, quickly and easily switch between one object to another, and between one type of object to other object.

Few patents disclose MRI devices with multiple apertures in the magnet structure. Hence, U.S. Pat. No. 5,490,513 discloses a medical magnetic resonance imaging system comprising: (a) a magnet having an imaging volume and at least two apertures thereto, each of the apertures providing patient access to the imaging volume; (b) at least two patient handling systems, each of the patient handling systems comprising a motorized and remotely-controlled bed structure which accesses a respective one of the apertures of the magnet, each of the bed structures having means for positioning the breast region of a respective patient for a magnetic resonance imaging procedure in the imaging volume of the magnet; (c) a radio frequency antenna system for transmitting radio frequency energy into each of the respective patients when in the imaging volume, and detecting magnetic resonance imaging data from the breast region of each the patient; and (d) automatic patient sequence control means for automatically sequencing the transfer of the respective patients into and out of the imaging volume. Likewise, U.S. Pat. No. 5,623,927 discloses a medical magnet resonance imaging system comprising: (a) a magnet having an imaging volume and at least two apertures, wherein each aperture is sufficiently large to provide patient access to the imaging volume; (b) at least two patient handling systems, with each of the patient handling systems comprising a moveable bed structure having means which provides access to one of the apertures of the magnet and with each of the moveable bed structures having means for receiving and positioning the breast region of a patient to be subjected to a magnetic resonance imaging procedure in the imaging volume of the magnet; (c) a radio frequency antenna system for transmitting radio frequency energy into a patient and detecting magnetic resonance imaging data from the breast region of each the patient. Scanned objects according to those patents are not maneuverable within the MRI device. Fine tuning of the various shape, size and type objects, especially in laboratory routine, wherein a frequent switching of scanned objects of different type shape and size is practically impossible utilizing those MRI systems.

None of the above provides a simple solution for routine insertion of more than one maneuverable small and tangible objects, such as laboratory items (microplates laboratory animals etc), within a single lab-scale experimental MRI device. Hence an MRI device with a plurality of individually controllable entry ports and MRI-compatible inserts therefor fulfill a long felt need.

BRIEF SUMMARY

It is thus one object of the invention to disclose an animal handling system

There is provided in accordance with a preferred embodiment of the present invention an MRD device including a first input port having a first cross-sectional area, and a second input port having second cross-sectional area, the first input port is substantially diametrically opposite the second input port.

Further in accordance with a preferred embodiment of the present invention, the first cross-sectional area is less than the second cross-sectional area.

Still further in accordance with a preferred embodiment of the present invention the first cross-sectional is different from the second cross-sectional area.

There is provided, in accordance with another preferred embodiment of the present invention, an animal handling system for use in an MRD device including: a first elongated enclosure having a proximal end, a distal open end and a first geometry, and a second first elongated enclosure having a proximal end, a distal open end and a second geometry. The first geometry includes a first cross-sectional area which is larger than a second cross-sectional area of the second geometry. The first elongated enclosure is inserted into a first input port of the MRD device and the second elongated enclosure is inserted in a second input port of the MRD device diametrically opposite to second input port, such that on insertion of the first elongated enclosure into the first input port and insertion of the second elongated enclosure into the second input, the second elongated enclosure slides into the first elongated enclosure through the open distal end of the first elongated enclosure.

Further, in accordance with another preferred embodiment of the present invention, the first elongated enclosure includes at least two portions, the at least two portions are telescopic.

Still further in accordance with another preferred embodiment of the present invention the proximal end of the first elongated enclosure is sealed against a circumferential edge of the first input port and the proximal end of the second elongated enclosure is sealed against a circumferential edge of the second input port thereby sealing the first and second elongated enclosures from the outside environment.

Additionally in accordance with another preferred embodiment of the present invention a mammal for experimenting is inserted into the second elongated enclosure.

Furthermore in accordance with another preferred embodiment of the present invention the first elongated enclosure includes a reaction testing device.

Further in accordance with another preferred embodiment of the present invention the mammal is selected from the group consisting of a rodent, a cat, a dog, a rabbit and laboratory experimental animals.

DETAILED DESCRIPTION

The following description is provided in order to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for routine handling and scanning of items in a single MRD.

The term 'Magnetic Resonance Device' (MRD) specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) spectroscope or any combination thereof. The MRD hereby disclosed is optionally a portable MRI device, such as the ASPECT Magnet Technologies Ltd commercially available devices, or a commercially available non-portable device. Moreover, the term 'MRD' generally refers in this patent to any medical device, at least temporary accommodating an anesthetized animal.

As used herein, the term "animal" or "mouse" generally refers in an interchangeable manner to any living creature, such as neonates, other mammal such as mice, rats, cats, dogs, rabbits etc and laboratory animals.

As used herein, the term "object" generally refers to items to be scanned, and include, in a non-limiting manner, laboratory items, such as nicroplates, microwells, tubes, veils, Eppendorf™ tubes and the like, animals, organs, tissues, reaction solutions, cell media, organic or inorganic matter and compositions thereof etc.

As used herein, the term "plurality" refers in a non-limiting manner to any integer equal or greater than 1.

Figure 1:
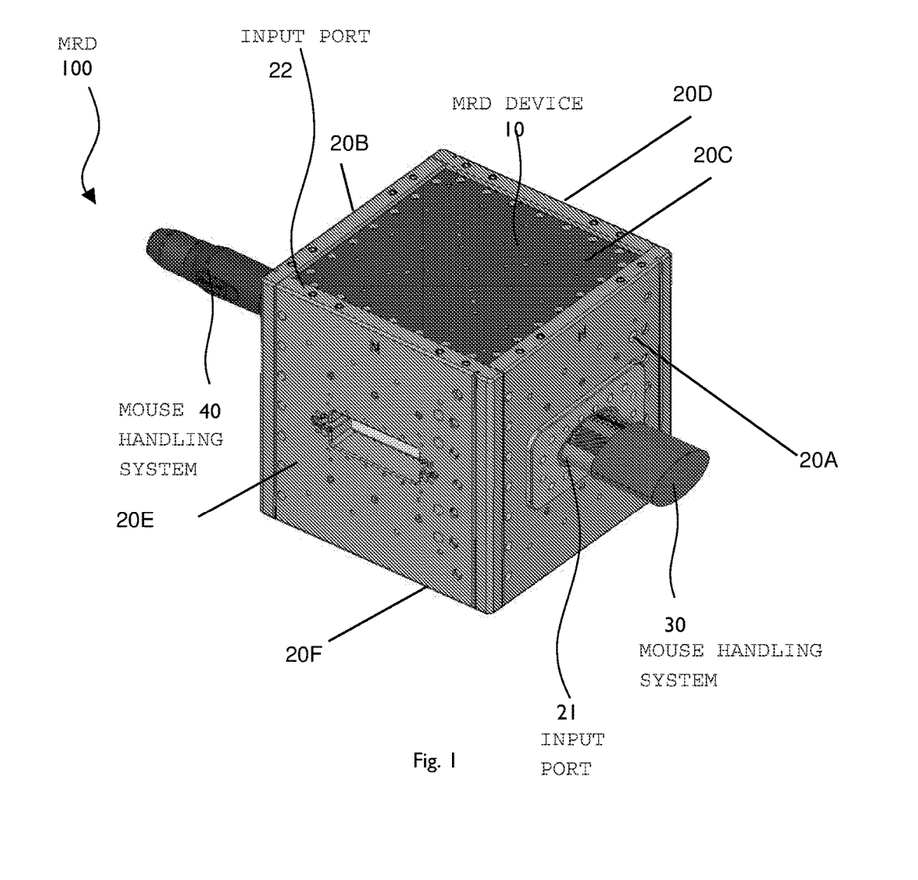
FIG. 1 shows an MRD device including two or more Mouse Handling Systems (MHS), in accordance with a preferred embodiment of the present invention.

Reference is now made to FIG. 1, schematically illustrating in an out-of-scale manner an MRD 100, here for example, a lab-scale MRI device. The MRD 100 includes a first wall 20a, a second wall 20b, a third wall 20c, a fourth wall 20d, a fifth wall 20e, and a sixth wall 20f. The first wall 20a includes a first input port 21. The second wall 20b includes a second input port 22. A plurality of mouse handling systems (MHS, 30, 40, FIGS. 3-4 and FIGS. 5-6, respectively) are shown reversibly inserted in the input ports, 21 and 22, respectively. The two MHS devices 30 and 40 are of different size and shape, enabling the MHS devices 30 and 40 to be inserted and manipulated when imaging or scanning different types of objects with the MRD. Only one of the MHS devices 30 and 40 is inserted into the magnetic resonance imaging space that exists between the walls of the MRD at a time, as shown by FIGS. 3 through 6. The number of walls of the MRD that the magnetic resonance imaging space exists between may range from two walls (See FIGS. 3 through 6) through six walls (i.e. See FIGS. 1 and 2).

Figure 2:
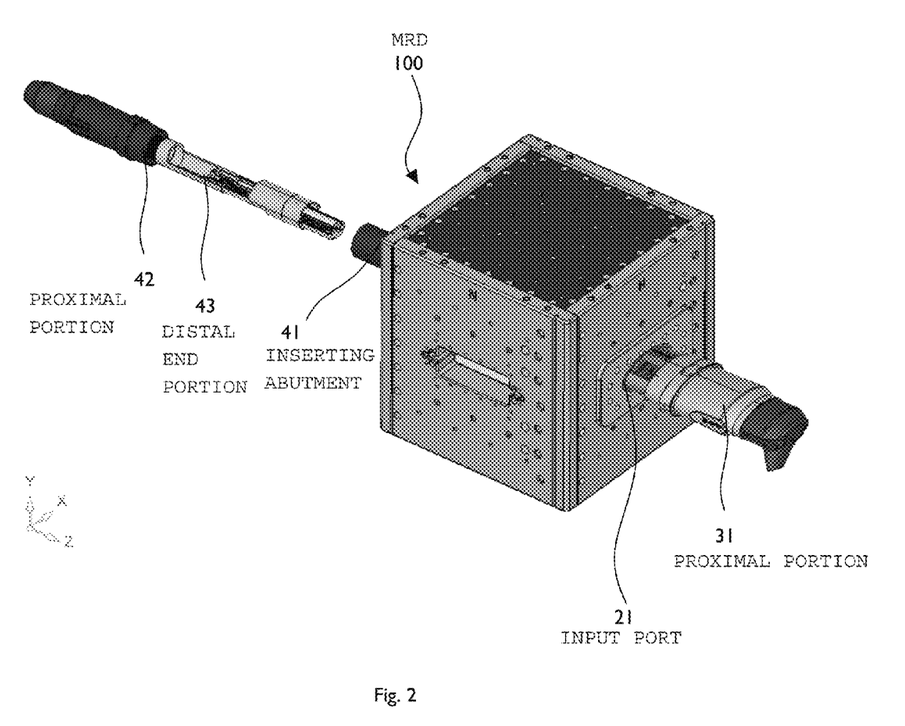
FIG. 2 shows the two Mouse Handling Systems (MHS), in accordance with a preferred embodiment of the present invention.

Reference is now made to FIG. 2, schematically illustrating in an out of scale manner MHS 30 and MHS 40. FIG. 1 shows that the MHS 30 has an ellipsoidal cross-section and the MHS 40 has a circular cross-section. Typically, the circular cross-sectional area of MHS 40 is less than the cross-sectional area of the MHS 30. According to the illustrated embodiment of the invention, both the MHS 30 and the MHS 40 are maneuverable elongated devices. Each one of the MHS' is characterized by a proximal end portion, which is located outside of the MRD 10 and possibly comprising an inserting abutment 41. At a distal end portion 43, the objects to be scanned are immobilized in a predefined configuration. The maneuverable MHS' 30 and 40 are rotatable about and translationally moveable parallel to the main longitudinal axis of shafts.

Figure 3:
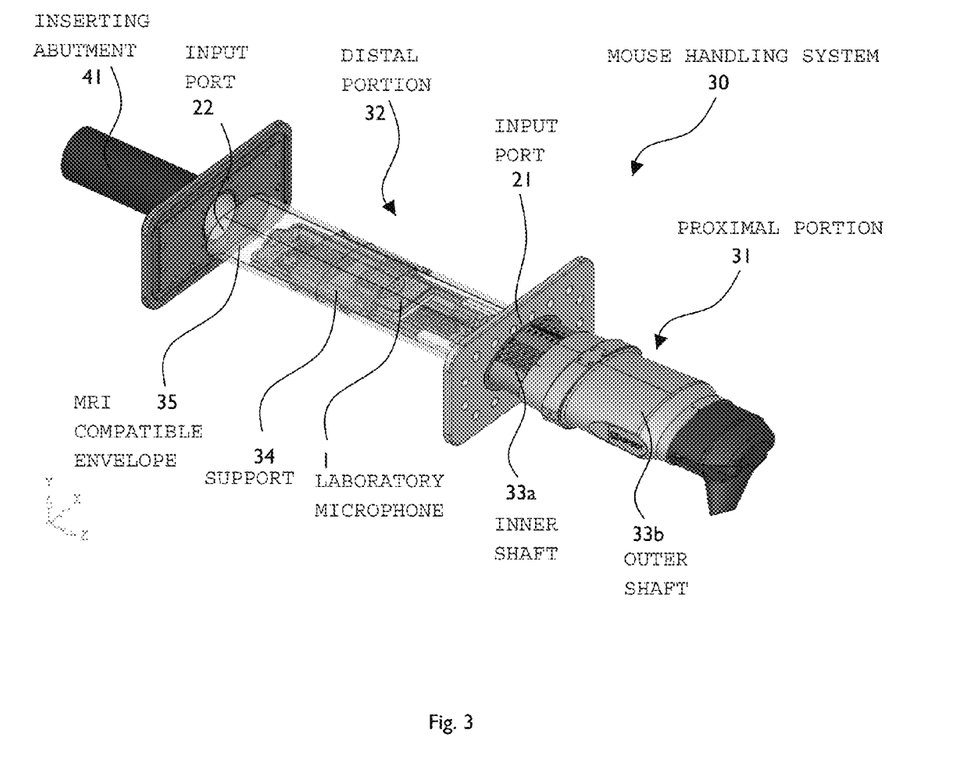
FIGS. 3 and 4 show the details of a view of the MHS device with an ellipsoidal cross-section.

Reference is now made to FIG. 3, schematically illustrating in an out of scale manner a detailed view of the MHS 30. The proximal portion 31 comprises, inter alia, at least one inner shaft 33a and at least one outer shaft 33b, both providing a telescopic maneuvering mechanism of the distal portion 32, located in proximity to an opening 21, within the MRI. The distal portion 32 is thus positioned, communicated with, and supplied with by means of the maneuverable proximal portion 31. Distal portion comprises a support 34, typically of ellipsoidal cross-section and includes a laboratory microplate I. The microplate I includes, inter alia, a plurality micro-wells, which contain reaction media to be scanned. According to this embodiment of the invention, the distal portion 32 is at least partially covered by an MRI-compatible envelope 35, thereby preventing leakage of hazardous materials and fluids to flow outside of the MRI towards an MRI operator and the laboratory ambient environment.

Figure 4:
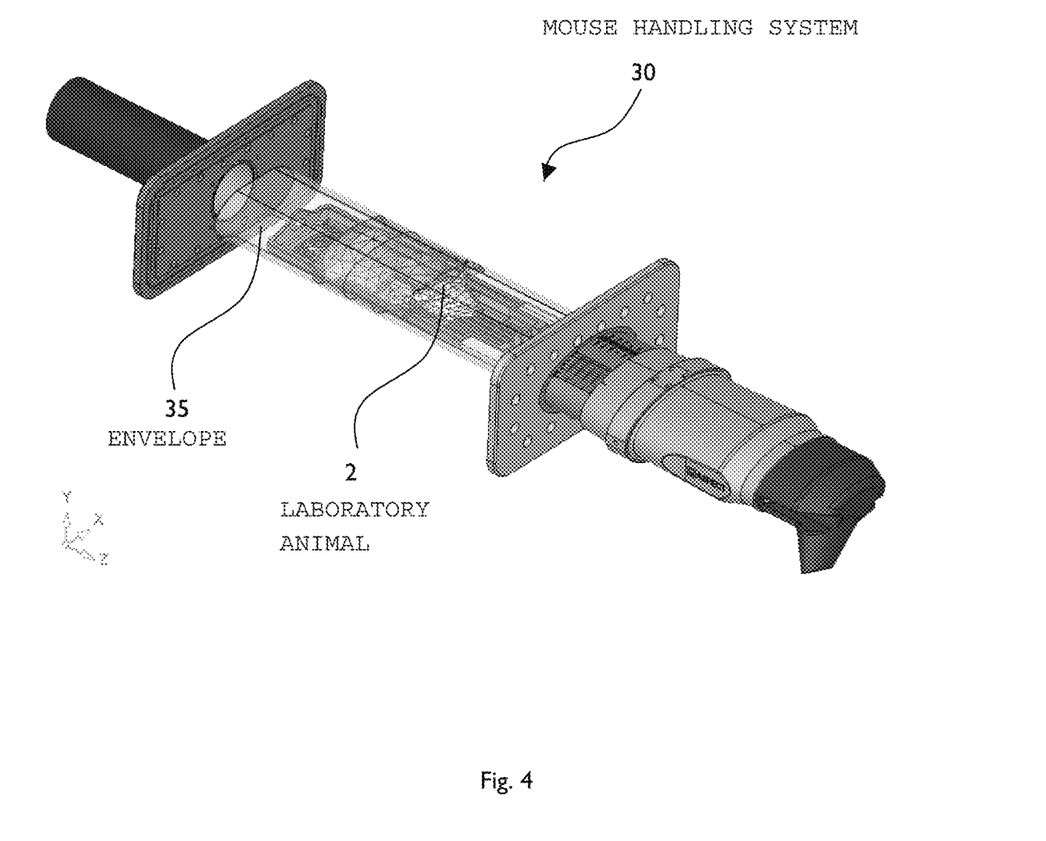

Reference is now made to FIG. 4, similarly illustrating in an out of scale manner a detailed view of the MHS 30. FIG. 4 shows that the item to be scanned is a laboratory animal 2, such as, a rat.

Figure 5:
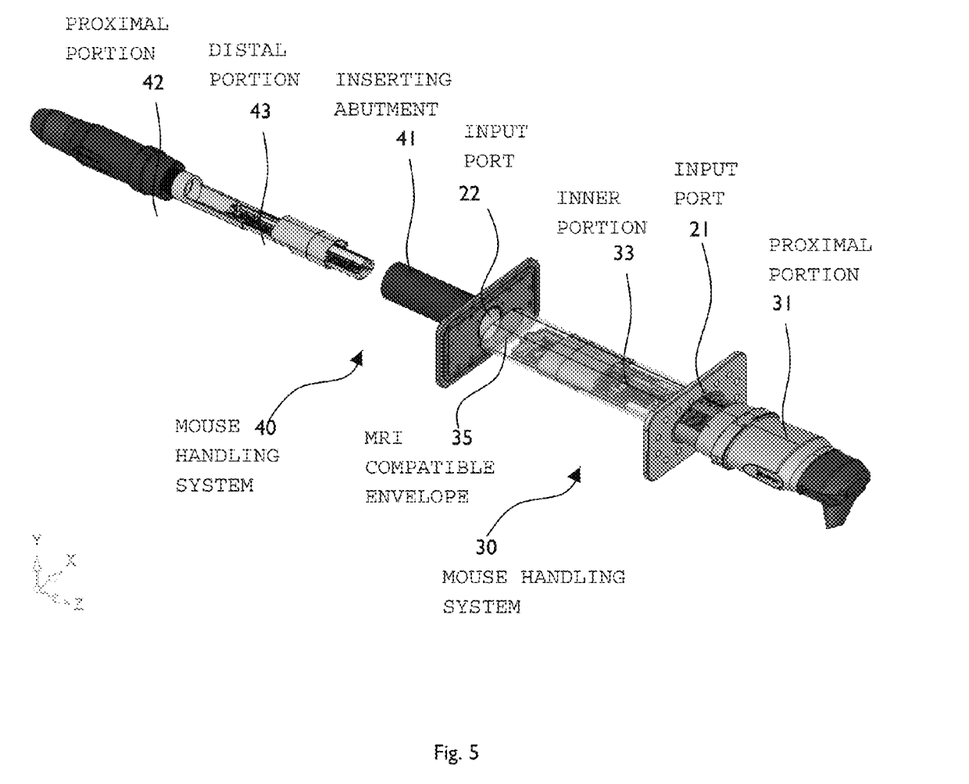
FIGS. 5 and 6 show the details of a view of the MHS device with a circular cross-section.

Reference is now made to FIG. 5, schematically illustrating in an out of scale manner a detailed view of MHS 30 and MHS 40. The MRI device 10 is schematically presented by means of the two opposite input ports 21 and 22. It is acknowledged in this respect that multiple input ports can be located in a relatively opposite orientation or in a relatively perpendicular orientation. FIG. 5 shows the easy and quick manner in which different types of MHSs are interchangeable. As described above, and according to the aforesaid embodiment of the invention, MHS 30 is inserted in the MRI device 100 via the input port 21. The location of the distal portion 32 is controlled from the proximal portion 31. An ellipsoidally-shaped cover 35 envelops an inner portion 33 of the MHS 30. The MHS 40 is inserted into input port 22 such that a distal portion 43 is located within an abutment 41 and coupled to the input port 22. The insertion of the MHS 40 into the MHS 30 is thus easily performed.

Figure 6:
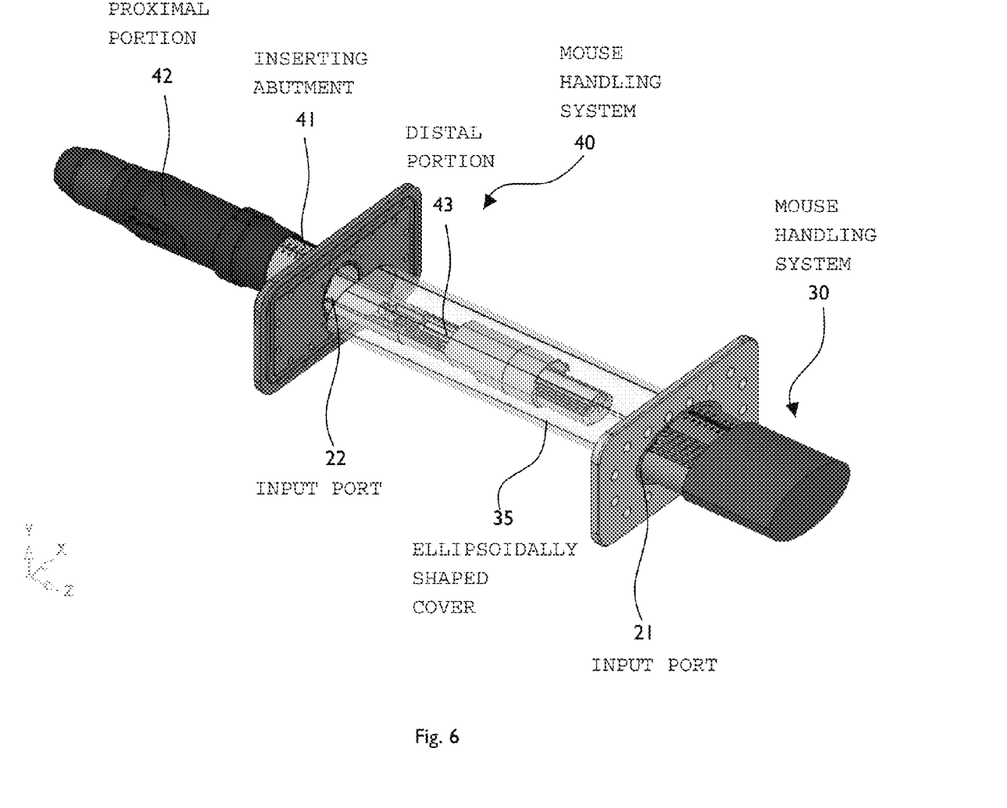

Reference is made to FIG. 6, schematically illustrating in an out of scale manner a detailed view of MHS 40 having a circular cross section which is typically less than that of the cross-section of the MHS 30. The MHS 40 is inserted via input port 22 to within the MRI device 10. A proximal portion 42 manipulates a distal portion 43. It is noticeable that 43 is inserted and encapsulated by the envelope 35. An inserting abutment for MHS 30 seals input port 21.

Hence, both means and methods for routine handling and scanning of items in a single MRI device is disclosed and presented.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

The invention claimed is:

1. A magnetic resonance device (MRD) having at least two walls and two input ports configured to perform magnetic resonance imaging (MRI) of a non-human animal, the MRD comprising:
a first input port positioned on a first wall of the at least two walls of the MRI MRD, the first input port having a first cross-sectional area configured to receive a first elongated enclosure of an animal handling system, into a magnetic resonance imaging space existing between the at least two walls of the MRI MRD enabled by the first elongated enclosure of the animal handling system having the first cross-sectional area of the first input port;
a second input port positioned on a second wall of the at least two walls of the MRI MRD, the second input port having a second cross-sectional area configured to receive a second elongated enclosure of a second animal handling system, into the same magnetic resonance imaging space existing between the at least two walls of the MRI MRD, enabled by the second elongated enclosure of the second animal handling system having the second cross-sectional area of the second input port;
wherein the first wall of the MRI MRD has a first surface that faces a first surface of the second wall of the MRI MRD,
wherein said first input port is substantially opposite said second input port, with the first cross-sectional area and the second cross-sectional area having different sizes from one another,
wherein the first cross-sectional area is large enough to accommodate a first non-human animal and the second cross-sectional area is large enough to accommodate a second non-human animal,
wherein the first non-human animal and the second non-human animal being selected from the group of: a rodent a mouse, a cat, a dog or a rabbit;
wherein only one of the elongated enclosures of either the first or second animal handling system may be inserted into the magnetic resonance imaging space existing between the at least two walls of the MRI MRD, at a time;
wherein the first input port and the second input port are positioned such that when either the first elongated enclosure of the animal handling system or the second elongated enclosure of the animal handling system is inserted into respectively the first input port or the second input port, a non-human animal, located within either the first or second elongated enclosure of the animal handling system becomes positioned, within the magnetic resonance imaging space existing between the at least two walls of the MRI MRD, enabling an imaging of the non-human animal when a MRI scan is conducted that utilizes the MRD.

2. The MRD device according to claim 1, wherein said first cross-sectional area of the first input port and first elongated enclosure of a first animal handling system is less than said second cross-sectional area of the second input port and second elongated enclosure of the second animal handling system.

3. The MRD device according to claim 1, wherein said first cross-sectional of the first input port and first elongated enclosure of a first animal handling system is also different in shape from said second cross-sectional area of the second input port and second elongated enclosure of the second animal handling system.

4. The MRD device according to claim 1 wherein the MRD device is portable from one location to another.

* * * * *